(12) United States Patent
Glazman

(10) Patent No.: US 7,823,586 B2
(45) Date of Patent: Nov. 2, 2010

(54) PERSONAL RESPIRATORY PROTECTION SYSTEM

(76) Inventor: Mark Glazman, 2725 Floribunda Dr., Columbus, OH (US) 43209

(*) Notice: Subject to any disclaimer, the term of this patent is extended or adjusted under 35 U.S.C. 154(b) by 657 days.

(21) Appl. No.: 11/782,887

(22) Filed: Jul. 25, 2007

(65) Prior Publication Data
US 2009/0025716 A1 Jan. 29, 2009

(51) Int. Cl.
A61M 11/00 (2006.01)
(52) U.S. Cl. .............. 128/201.25; 128/201.22; 128/202.25; 2/171.3
(58) Field of Classification Search ..............
128/201.22–201.29, 205.25–205.29, 206.17, 128/206.21; 2/171.3, 410, 5, 6.6
See application file for complete search history.

(56) References Cited

U.S. PATENT DOCUMENTS

| 3,881,478 | A | * | 5/1975 | Rosendahl et al. ..... 128/200.28 |
| 4,280,491 | A | | 7/1981 | Berg et al. |
| 4,462,399 | A | | 7/1984 | Braun |
| 4,488,547 | A | | 12/1984 | Mason |
| 4,899,740 | A | | 2/1990 | Napolitano |
| 4,965,887 | A | | 10/1990 | Paoluccio et al. |
| 5,125,402 | A | | 6/1992 | Greenough |
| 6,014,971 | A | | 1/2000 | Danisch et al. |
| 6,250,299 | B1 | | 6/2001 | Danisch et al. |
| 6,279,572 | B1 | | 8/2001 | Danisch et al. |
| 6,370,695 | B2 | * | 4/2002 | Paris et al. .................. 2/171.3 |
| 6,760,925 | B1 | * | 7/2004 | Maxwell ..................... 2/171.3 |
| 6,925,655 | B1 | * | 8/2005 | Maki et al. .................. 2/171.3 |
| 6,941,949 | B2 | | 9/2005 | Amante et al. |
| 6,945,249 | B2 | | 9/2005 | Griesbach, III et al. |
| 7,036,502 | B2 | | 5/2006 | Manne |
| 7,118,608 | B2 | | 10/2006 | Lovell |
| 7,143,451 | B2 | | 12/2006 | Lundgren |
| 7,275,535 | B1 | * | 10/2007 | Brockman ............. 128/201.25 |
| 7,331,064 | B1 | * | 2/2008 | Quintal ..................... 2/209.13 |

* cited by examiner

Primary Examiner—Steven O Douglas
(74) Attorney, Agent, or Firm—David L. King

(57) ABSTRACT

A respiratory protection system which is worn by a passenger during a flight in air plane, by a patient visiting hospital or doctors office, a nurse working with a patient during hospital stay, or the like. The system includes a relatively light weight, substantially rigid, headgear structure, containing an air disinfection chamber, a fan means, a filter means, an ultraviolet air disinfection means, an air blanket origination means and an energizing means.

10 Claims, 3 Drawing Sheets

PERSONAL RESPIRATORY PROTECTION SYSTEM

FIELD OF THE INVENTION

This invention is related personal health protection systems in general, and to personal respiratory protection systems having a headgear which is worn by an individual and protect an individual from airborne infections and hazards.

BACKGROUND OF THE INVENTION

The airborne transmission of bacteria and viruses, chiefly respiratory disease organisms is a serious problem in health care. The control of airborne disease transmission has become increasingly important with an increasing number of people traveling in air plains, trains, buses and cars sitting in close proximity to each other.

This coupled with risk of pandemic influenza have created a need for inexpensive, efficient personal respiratory protection system (air purification system). The risk of contracting of air born infections can be reduced by the protection of respiratory organs and eyes from airborne microorganisms along with providing purified air for breathing.

Air purification could be achieved by killing the infectious microorganism by ultraviolet (UV) radiation. Ultraviolet radiation to destroy airborne microorganisms can be used inside of small chamber.

The spread of air borne infections indoors could be controlled by proper ventilation and also by means of personal protection such respirators. Center of Disease Control and Prevention recommends that protection means such a respirators " . . . should only be used as a "last line of defense" when engineering control systems are not feasible. Engineering control systems, such as adequate ventilation or scrubbing of contaminants should be used to negate the need for respirators".

The high risk of spread of tuberculosis (TB) infection and other airborne disease during long transcontinental or local flights along with the risk of airborne infections in modern health institutions and correctional institutions indicates however, that the known air purification systems are inadequate in controlling the spread of airborne microorganisms.

There are a number of means which reduce risk of contracting of airborne infection. Among these means are different types of masks and protective gear. The U.S. Pat. Nos. 6,941,949; 6,945,249; 4,488,547 disclosed the examples of face masks.

The disadvantage of protective masks is that they should have proper fit to each wearer. Care should be taken to provide each wearer with a mask that fits properly. This usually can be accomplished only by individual fittings and fit tests. Other disadvantages of face masks include resistance to breathing and need for frequent replacement of air-purifying elements or disposable masks itself.

The masks can provide significant protection against bacteria and spores but have low effectiveness against viruses.

Better degree of protection could provide powered air-purifying respirators. Powered air-purifying respirators provide an airstream to the wearer. U.S. Pat. No. 4,899,740 discloses powered air-purifying respirator system for supplying clean, breathable air to a hood or face mask.

The system can be carried on a waist belt and includes a housing containing air inlet and outlet plenums, and a battery powered, electric motor operated blower connected between the inlet and outlet plenums. PAPR which include hoods and helmets are commonly worn in environments where the air contains contaminants.

Supplied air helmets have a fluid impermeable visor that is located in front of the wearer's face. The visor has a transparent window that allows the wearer to see the surroundings. A face seal is attached to the visor to separate a breathing zone or an interior gas space from the surrounding exterior gas space. U.S. Pat. Nos. 6,014,971, 4,462,399, and 4,280,491 disclose examples of supplied air helmets.

Disadvantages of these PAPR include weight, bulk, complex design, the need for continual maintenance, at least daily replacement of air-purifying elements, and periodic replacement of batteries and blowers. Another disadvantage of masks and protective gear is uncomfortable feeling and sense of isolation from the environment.

There are known other respiratory protection devices for protecting the wearer against inhalation of air-borne particulate matter by creating a high velocity air curtain enclosing the wearer's face. U.S. Pat. Nos. 3,881,478, 7,036,502, and 4,280,491 disclose examples of respiratory protection creating air curtain enclosing wearers face. These devices do not create a sense of isolation. The disadvantages of these devices are their bulk and complex design, and their inability to control viruses. Another shortcoming of the helmet disclosed in U.S. Pat. No. 3,881,478 is the requirement of an air supply from a separate source of clean air. The U.S. Pat. No. 7,036,502 discloses the headset creating a curtain of air across the face. This device has a fan which provides the air supply for the air curtain.

However, the device according to the U.S. Pat. No. 7,036,502 is not convenient for nor adapted to, nor does it address, the matter of providing respiratory protection for the passengers of an airplane or nurses in a hospital or people walking on the streets. According to the U.S. Pat. No. 7,036,502, the headset has a boom with affixed to the boom fan and tubing. According to the U.S. Pat. No. 7,036,502 in addition to the fan and the tubing, the conditioning means are also affixed to the boom. Significant weight of the means of air conditioning makes the moment of force excessive and requires additional means of support affixed to the shoulders or to the neck to keep the headset on the head of the wearer. The boom and an additional means of support, hence, does not lend itself to any kind of "walk-about" portability, which presents operational requirements for the airplanes, hospital or other public places that the device according to the U.S. Pat. No. 7,036,502 had not sought to meet. Further, the device according to the U.S. Pat. No. 7,036,502 cannot be safely used in any situation where people are in close proximity to each other, like an airplane or a hospital or a crowd. The means of directing air flow insures that the breath of the wearer of the device is directed toward the faces of other individuals on the left or the right of the wearer. Any infectious microbes carried by that individual would thus be blown toward the faces of the individuals to the right or the left. The blowing of microbes towards other individuals is counter productive to the idea of protecting individuals from air borne disease.

A variety of air filters have been designed for providing a purified air into supply helmet and further into breathing zone. These filters could used alone or as a sequence of packed bed filter media packets having filter media therein of specifically targeted types that will capture dangerous to human health air pollutants. Examples of air filters for personal air purifiers and helmets are shown in U.S. Pat. Nos. 7,118,608, 6,279,572B1, 6,250,299B1, 6,014,971, 5,125,402, 4,965,887, 4,462,399.

While known personal respiratory protection systems have provided a variety of constructions for establishing a separation between the interior gas space and the surrounding contaminated environment, and for providing a filtered air into the interior space, these known products have not been fashioned to enable a protection from airborne viruses, to improve comfort, and reduce a burden of continual maintenance.

The known products are bulk, have visible solid protective boundaries, which make them uncomfortable for use in an airplane, a hospital, an office or other general environment in which air could be contaminated with infectious microbes.

SUMMARY OF THE INVENTION

A respiratory protection system which is worn by a passenger during a flight in air plane, by a patient visiting hospital or doctors office, a nurse working with a patient during hospital stay, or the like.

The system includes a relatively light weight, substantially rigid, headgear structure, containing an air disinfection chamber, a fan means, a filter means, an ultraviolet air disinfection means, an air blanket origination means and an energizing means.

The air disinfection chamber is mounted preferably at the upper part of the headgear. The air disinfection chamber has air impenetrable walls, an air inlet for environmental air at one end and an air outlet for disinfected air at the opposite end.

The fan means has at least one fan mounted in the headgear structure. The fan means connected with the air disinfection chamber, and with the air blanket origination means to generate air flow through the air disinfection chamber and to provide continuous air flow of disinfected air for the air blanket. The fan means preferably mounted at said air disinfection chamber.

The ultraviolet air disinfection means mounted at said air disinfection chamber. These ultraviolet air disinfection means are having a source of germicidal beams, and a surrounding reflecting means transforming the germicidal beams in substantially collimated array of germicidal beams.

An energizing means electrically connected with the air disinfection means and the fan means to provide the energy for said air disinfection means and for said fan means.

The air blanket origination means, to form an air blanket of the disinfected air to protect the eyes and respiratory system of the wearer. The air blanket origination means preferably located below of said air disinfection chamber, to direct of the airflow of disinfected air along the face of the wearer.

A filter means in said headgear construction to provide filtering the air through said filter means, and comprising of a general filter for filtering all said air flow and a lamp filter to keep said source of germicidal beams clean.

The headgear construction is attached to an internal, adjustable headband. The headband includes straps for specifically adjusting the size thereof to the wearer. A replaceable liner, said liner removable attachable to said headgear construction. A housing means for supporting said disinfection chamber.

The system also includes a shroud which is adapted to be attached to or draped over the headgear construction to completely cover the construction in order to maintain casual headgear appearance. The shroud has at least one air inlet containing the filter which is, arranged to be located adjacent to the fan in the headgear construction.

Preferably the personal respiratory protection system has ultraviolet lamp emitting germicidal radiation towards the airflow.

Preferably the personal respiratory protection system has the light emitting diode. The light emitting diode sends a flux of germicidal radiation towards the airflow.

Preferably the personal respiratory protection system has the ultraviolet lamp enclosed in a substantially parabolic reflector, the reflector having an aperture for passing filtered air towards the lamp.

Preferably the personal respiratory protection system has a source of germicidal irradiation producing substantially collimated germicidal beams.

Preferably the personal respiratory protection system has said source of germicidal radiation. The source of germicidal radiation is situated at the inlet end of the chamber. The source of germicidal emits germicidal beams towards said outlet end of the chamber.

Preferably the personal respiratory protection system has the source of germicidal radiation situated at one sidewall of the chamber and emitting the germicidal beams towards another sidewall of the chamber.

Preferably the personal respiratory protection system has the general air filter. Preferably the personal respiratory protection system has the battery located in the headgear. The battery energizes said sources of germicidal radiation and said fans.

Preferably the personal respiratory protection system has the battery located outside of headgear and connected with fan means and the source of the germicidal radiation by flexible cord.

BRIEF DESCRIPTION OF THE DRAWINGS

The invention will be described by way of example and with reference to the accompanying drawings in which.

DETAILED DESCRIPTION OF THE INVENTION

Figure 1:
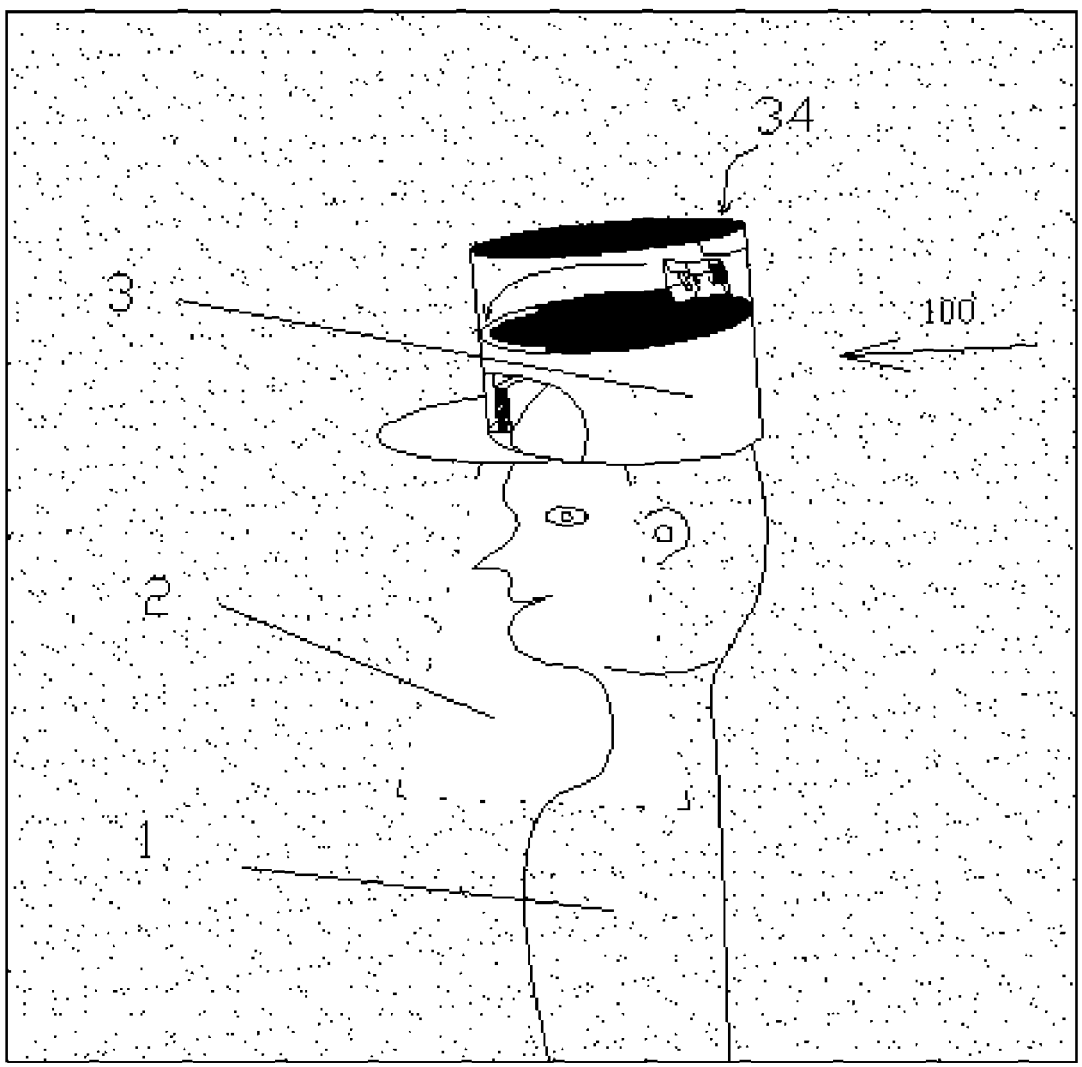
FIG. 1 is a schematic view of a preferred embodiment of the invention showing a personal respiratory protection system which is worn by a person with a partially cutaway view to expose the components of the personal respiratory protection system.
Figure 2:
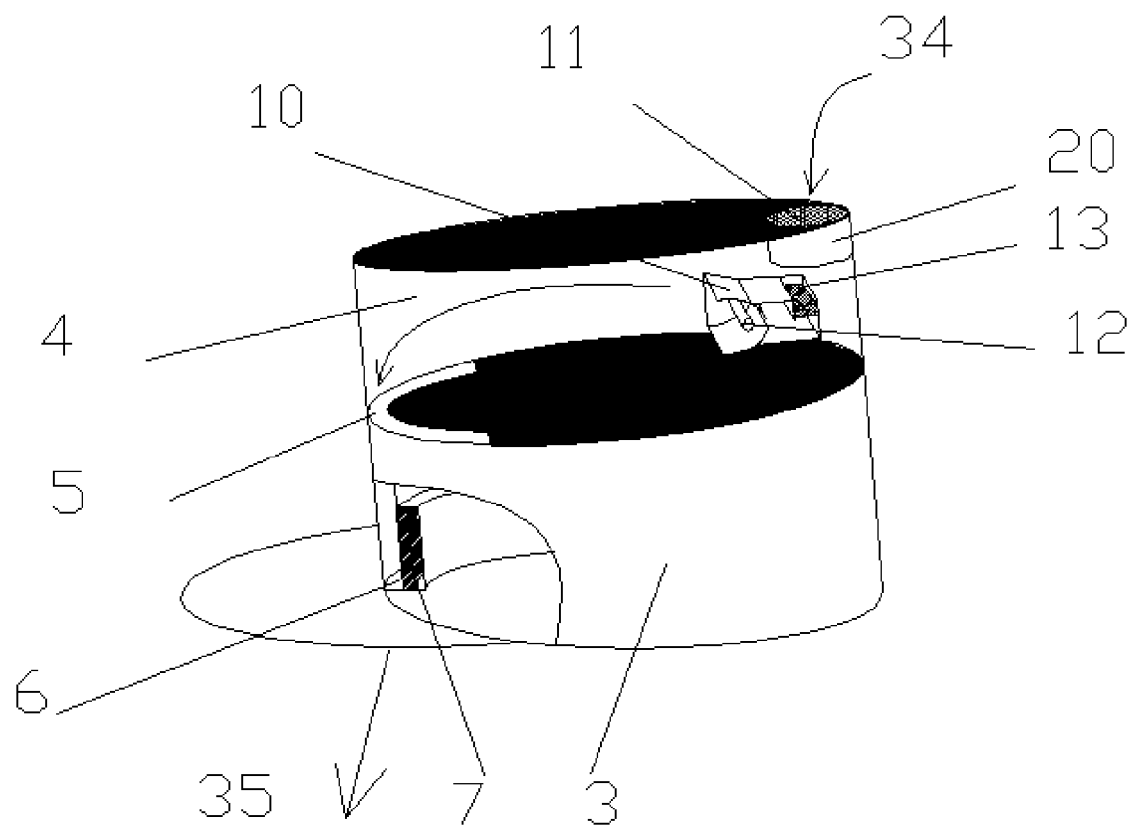
FIG. 2 is a schematic view of a preferred embodiment of the invention showing a personal respiratory protection system and all its components.
Figure 3:
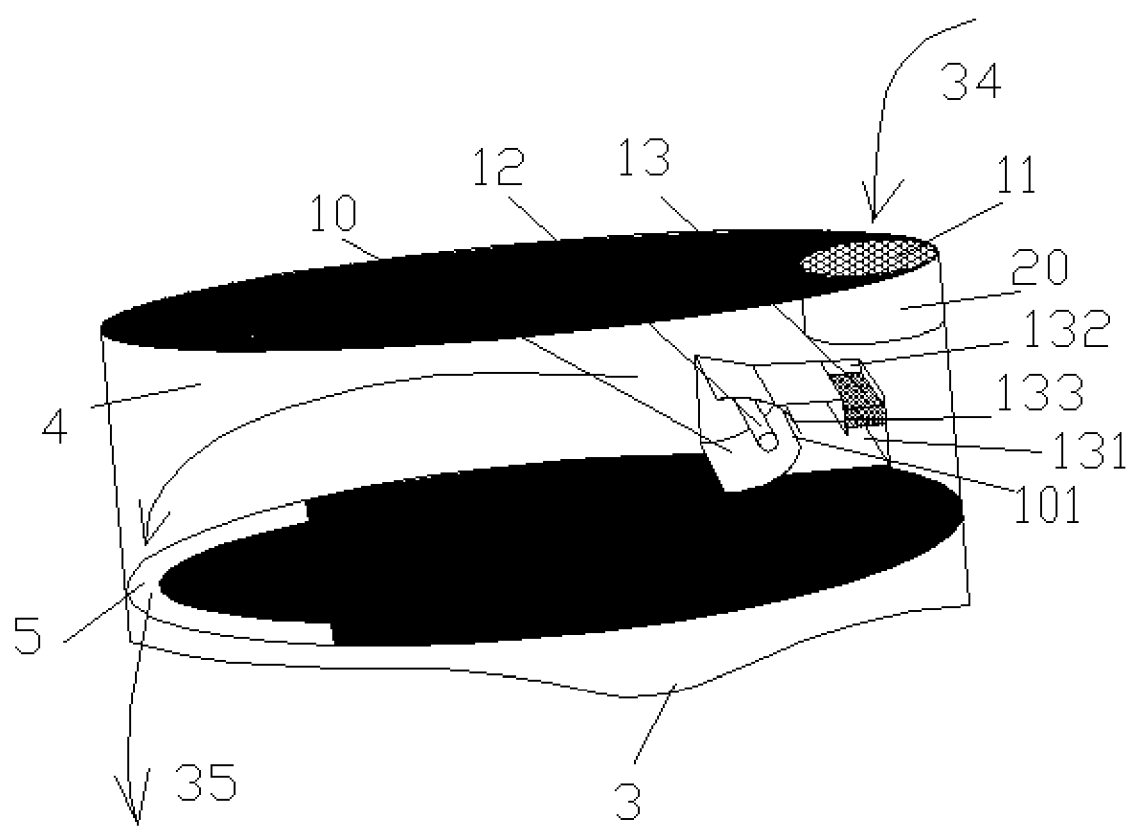
FIG. 3 is a schematic view of a preferred embodiment of the invention showing a cross sectional view of air disinfection chamber and its components.

The present invention provides a personal respiratory protection system which is worn by a person, generally referred to by reference 100. The preferred embodiment of the invention is shown in FIG. 1, FIG. 2 and FIG. 3.

The personal respiratory protection system 100 includes the relatively light weight, substantially rigid, headgear construction 3, containing the air disinfection chamber 4. The air disinfection chamber 4 is mounted at the upper part of the headgear construction 3. The air disinfection chamber 4 has the air inlet 11 at one end and the air outlet 5 at the opposite end. The fan 20 is mounted in the headgear construction 3 and connected with the air disinfection chamber 4.

The ultraviolet air disinfection means includes the ultraviolet lamp 12 and reflector 10. The ultraviolet lamp 12 and reflector 10 are mounted at the air disinfection chamber 4. The ultraviolet lamp 12 is located inside of the cavity of the reflector 10. As shown, the reflector 10 is substantially parabolic over most of its surface. At the extremities the surface may be elliptical.

The reflector 10 has an aperture 101. The reflector 10 contacts at the aperture 101 location the external surface of the dust free chamber 131 creating a close fitting arrangement. The reflector 10 is attached to the headgear construction 3 by means of threaded fasteners.

According to the preferred embodiment the axis of the ultraviolet lamp 12 is situated in the focal line of the parabolic reflector 10 by the lamp holder 15 (not shown). The lamp holder 15 is mounted at the sidewall of the parabolic reflector 10. The parabolic reflector 10 is installed such that its axis or axis plane is substantially parallel to the direction of the air flow inside of the air disinfection chamber 4. The reflector 10 is transforming the radiation from ultraviolet lamp 12 into substantially collimated array of germicidal beams.

According to the preferred embodiment, the dust free chamber 131 includes the input opening 132, the output opening 133 and the filter 13 for passing the substantially dust free air flow into the dust free chamber 131 and further into the cavity of the reflector 10 to keep the ultraviolet lamp 12 clean.

The filter 13 is situated in the input opening 132. The output opening 133 is tightly connected with the reflector aperture 101.

Preferably the output opening 133 and the reflector aperture 101 are narrow, long slits extending along the entire length of the lamp 12.

The filter 13 is an effective particulate filter. In case of the air filtration the high efficiency particulate filters or electrostatic filter could be used but the application of other filters is not limited.

According to the preferred embodiment the battery 40, electrically connected to the ultraviolet lamp 12 and for the fan means 20, provide the energy for the ultraviolet lamp 12 and for the fan means 20. The battery 40 is mounted at the headgear construction 3.

According to the preferred embodiment the battery 40 is rechargeable.

According to another preferred embodiment the battery 40 is located outside of headgear and connected with fan means 20 and the ultraviolet lamp 12 by flexible cord.

According to preferred embodiment the fan means 20 mounted at the air disinfection chamber 4 by threaded fasteners. The fan means 20 generates the air flow through air disinfection chamber 4. The air flow 34 containing infectious microorganisms enters the air disinfection chamber 4; the disinfected air flow 35 leaves the air disinfection chamber 4.

According to the preferred embodiment, the air blanket origination means 6 located in the front part of the headgear construction 3. The air blanket origination means 6 directs of the disinfected airflow 35 along the face of the wearer to form an air blanket 2 of the disinfected air to protect the eyes and respiratory system of the wearer 1. The air blanket origination means 6 located below of the air disinfection chamber 4.

According to the preferred embodiment the filter means 11 located at the headgear construction 3 to provide filtering the air through said filter means.

The filter means 11 is an effective particulate filter. In case of the air filtration the high efficiency particulate filters or electrostatic filter could be used but the application of other filters is not limited.

The headgear construction is attached to an internal, adjustable headband 7. The headband includes straps for specifically adjusting the size thereof to the wearer. According to the preferred embodiment a replaceable liner is attached to said headgear construction.

The system also includes a shroud which is adapted to be attached to or draped over the headgear construction 3 to completely cover the headgear construction 3 in order to maintain casual headgear appearance. The shroud has at least one air inlet containing which is, arranged to be located adjacent to the fan 20 in the headgear construction.

Preferably the personal respiratory protection system has ultraviolet lamp 12 emitting germicidal radiation towards the airflow. Preferably the personal respiratory protection system has the light emitting diode. The light emitting diode sends a flux of germicidal radiation towards the airflow.

Preferably the personal respiratory protection system has the ultraviolet lamp 12 enclosed in a substantially parabolic reflector 10, the reflector having an aperture 101 for passing filtered air towards the ultraviolet lamp 12.

Preferably the personal respiratory protection system has the filter means 11 said filter means comprises distinct portions of said shroud means.

Preferably the personal respiratory protection system has the battery 40 located in the headgear construction 3. The battery energizes said sources of germicidal radiation and said fans.

Preferably the personal respiratory protection system has the battery 40 located outside of headgear and connected with fan means and the source of the germicidal radiation by flexible cord.

Preferably the personal respiratory protection system has a source of germicidal irradiation producing substantially collimated germicidal beams.

Preferably the personal respiratory protection system has said source of germicidal radiation. The source of germicidal radiation is situated at the inlet end of the chamber. The source of germicidal emits germicidal beams towards said outlet end of the chamber.

Preferably the personal respiratory protection system has the source of germicidal radiation situated at one sidewall of the chamber and emitting the germicidal beams towards another sidewall of the chamber.

In the present invention a protection of respiratory system of the wearer may be achieved. The protection may be achieved by placing the headgear on the head of the wearer and turning the system ON. The battery 40 will energize the fan 20 and the ultraviolet lamp 12.

The ultraviolet lamp 12, situated at the inlet end of the chamber and energized by battery 40, emits germicidal radiation. The parabolic reflector 10 is transforming the germicidal radiation into collimated array of beams going in the direction of the airflow, maximizing the absorption of the germicidal energy and germicidal efficiency. The walls of air disinfection chamber covered by material with high reflectivity for ultraviolet radiation to maintain germicidal efficiency. The fan 20 blows the air flow 34 of environmental air containing viruses and bacteria through the filter 11 into the air disinfection chamber 4. The filter 11 arrests large airborne particles. Small particles are passing the filter 11 and enter into air disinfection chamber 4. The air flow 34 being irradiated by sufficient amount of germicidal radiation in the air disinfection chamber 4. The irradiation kills the air borne microorganisms containing in the air flow 34. The treatment of the air flow 34 of environmental air containing viruses and bacteria in the air disinfection chamber 4 transforms the air flow 34 of environmental air containing viruses and bacteria into the disinfected air flow 35. The fan 20 forces the disinfected air flow 35 out of the air disinfection chamber 4 trough the air outlet 5. and further forces the disinfected air flow 35 to go through the air blanket origination means 6. The air blanket origination means 6 is having slit curved orifice which directs the airflow of disinfected air 35 down along the face of the wearer 1. Continuous air flow of disinfected air 35 via the slit curved orifice forms an air blanket 2 of the disinfected air. The air blanket 2 of the disinfected air covers the area around the face and protects the eyes and respiratory system of the wearer 1.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A personal respiratory protection system, comprising:
   a headgear construction modified to be mounted on the head of a wearer;
   an air disinfection chamber adapted to be mounted within said headgear construction and located in the space between the wearer's head and an outside surface of the headgear construction, said air disinfection chamber having an air inlet at one end and an air outlet at an opposite end;
   a fan means mounted at said air disinfection chamber, said fan means having a fan motor and blades to generate an air flow through said chamber;
   an ultraviolet air disinfection means mounted at said chamber to produce germicidal means for killing microorganisms in the air flow, the ultraviolet air disinfection means including a germicidal source to disinfect the air flow;
   a filter means in said headgear construction to provide filtering of the air flow through the filter means, the filter means including a general filter for filtering all of the air flow and a local filter to keep said germicidal source clean;
   an air blanket origination means located within said headgear construction and connected to said air disinfection chamber, to direct said airflow along the face of the wearer to form an air blanket of disinfected air to protect the eyes and respiratory system of the wearer;
   an energizing means, to provide the energy for said air disinfection means and for said fan means; and
   a replaceable liner, said replaceable liner being removable and attachable to said headgear construction.

2. The personal respiratory protection system recited in claim 1 wherein the germicidal source of irradiation is an ultraviolet lamp.

3. The personal respiratory protection system recited in claim 1 wherein the germicidal source of irradiation is a light emitting diode.

4. The personal respiratory protection system recited in claim 2 wherein the ultraviolet lamp is enclosed in a substantially parabolic reflector, the reflector having an aperture for passing filtered air towards the lamp.

5. The personal respiratory protection system recited in claim 1 wherein a germicidal source of irradiation is producing substantially collimated germicidal beams.

6. The personal respiratory protection system recited in claim 1 wherein, said germicidal source is situated at the inlet end of the chamber and emits germicidal beams towards said outlet end of the chamber.

7. The personal respiratory protection system recited in claim 1 wherein, the chamber has at least two sidewalls and said germicidal source is situated at one sidewall of the chamber and emits germicidal beams towards the other sidewall of the chamber.

8. The personal respiratory protection system recited in claim 1 wherein, the energizing means is a battery located in the headgear.

9. The personal respiratory protection system recited in claim 1 wherein, the energizing means is a battery located outside of headgear and connected to the fan means and the germicidal source of the radiation by a flexible cord.

10. The personal respiratory protection system recited in claim 1 wherein, a headgear construction has a replaceable liner, said replaceable liner being removable and attachable to said headgear construction.

* * * * *